United States Patent [19]

Acevedo

[11] Patent Number: 4,674,978
[45] Date of Patent: Jun. 23, 1987

[54] ORTHODONTIC APPLIANCE

[76] Inventor: Raul Acevedo, 6103 Castor Ave., Philadelphia, Pa. 19149

[21] Appl. No.: 870,633

[22] Filed: Jun. 4, 1986

[51] Int. Cl.⁴ .................................................. A61C 7/00
[52] U.S. Cl. ...................................................... 433/8
[58] Field of Search ................................... 433/8, 9, 11

[56] References Cited

U.S. PATENT DOCUMENTS

| | | | |
|---|---|---|---|
| 3,052,027 | 9/1962 | Wallshein | 32/14 |
| 3,218,714 | 11/1965 | Wallshein | 32/14 |
| 3,464,112 | 9/1969 | Silverman et al. | 433/11 |
| 3,922,787 | 12/1975 | Fischer et al. | 433/8 |
| 3,936,939 | 2/1976 | Faunce | 32/14 |
| 3,964,165 | 6/1976 | Stahl | 433/8 |
| 4,284,405 | 8/1981 | Dellinger | 433/8 |
| 4,470,809 | 9/1984 | Klepacki | 433/15 |
| 4,533,320 | 8/1985 | Piekarski | 433/9 |

Primary Examiner—Robert Peshock
Attorney, Agent, or Firm—Dann, Dorfman, Herrell and Skillman

[57] ABSTRACT

A wedge-shaped orthodontic appliance is described for affixation to the crown of the tooth of a patient. The appliance contains receiving slots in its thicker end for holding an archwire. A tapered end is provided to direct food bolus away from the archwire support area.

16 Claims, 7 Drawing Figures

ORTHODONTIC APPLIANCE

FIELD OF THE INVENTION

The invention relates to an improved orthodontic appliance of the type permitting mounting of an archwire to apply corrective forces to the teeth of a patient.

BACKGROUND AND PRIOR ART

The application of corrective forces to rearrange the teeth of patients for surgical and cosmetic purposes has been accomplished in a number of ways. One traditional method of orthodontic treatment consists of applying metallic band devices around the individual teeth of the patient. Affixed to the metal band in such devices is a bracket portion designed to receive an archwire, and the device may also contain additional apertures for receiving ligating wires for the purpose of affixing the archwire securely to the bracket. Normally, the archwire is rigidly affixed to the rear teeth, such that application of a force to the rear teeth will transmit the force, by way of the archwire, to the other teeth of the patient.

Problems may arise in using metallic band devices, for example when the teeth of a patient are tightly compacted. In some cases, it is necessary to remove one or more of the patient's teeth in order to put the metallic band devices around the remaining teeth. Application of metallic bands may also result in discomfort to the patient during their installation.

Due to such deficiencies, alternate methods of affixing orthodontic appliances to a patient's teeth have been developed. Specifically, orthodontic appliances have been developed for direct affixation to the exposed face of the patient's tooth, for example by using adhesive. Such devices are affixed to the enamel on the crown of the tooth, the term "crown" referring to the enamel-covered part of the tooth which is exposed beyond the gum. Orthodontic devices of this type have been constructed of, for example, plastic, metal or ceramic.

Orthodontic devices for attachment to the surface of the tooth may be mounted onto a protective support which itself is attached to the patient's tooth. For example, U.S. Pat. No. 3,936,939 discloses a veneer supported orthodontic appliance wherein the veneer portion is affixed to the patient's tooth using adhesive. The orthodontic appliance is molded into the veneer substrate and protrudes therefrom. The devices may also be rendered aesthetically pleasing. In U.S. Pat. No. 4,470,809, an orthodontic appliance for attachment to the tooth surface is formed of molded plastic material which is colored to resemble the natural color of human teeth.

It has also been suggested that a flexible orthodontic appliance would lessen the shock of the application of force to the teeth. An example of such a device, wherein a flexible bracket member is affixed directly to the tooth or onto a metallic band, is disclosed in U.S. Pat. No. 3,052,027.

During the shifting of teeth during their rearrangement by corrective forces, it is frequently desirable to achieve actual bodily movement of the teeth and not simply a tilting or tipping movement of the teeth, a result which is not achieved by the aforesaid devices. It has been found that if the corrective force exerted by the archwire is placed on the one-third of the crown of the patient's tooth nearest the gum, a more accurate and permanent corrective result may be achieved as the bone structure of the patient heals the teeth into their new arrangement.

It has also been found that during use of available orthodontic devices, including the above-mentioned devices affixed to the surface of the tooth, food tends to accumulate on or around the archwire and/or its supporting brackets. It would, therefore, be highly desirable to provide a configuration to the orthodontic appliance which discouraged or prevented the accumulation of food on the archwire and its support means, while maintaining effective utility and comfort to the wearer.

SUMMARY OF THE INVENTION

The present invention provides an orthodontic appliance for direct attachment to the front surface of a patient's tooth which applies the force of the archwire to the third of the crown of the patients teeth nearest the gum while effectively minimizing food accummulation adjacent the archwire and archwire brackets.

In accordance with the invention, an improved orthodontic appliance is constructed and designed for direct affixation to the exposed surface of a patient's teeth. It has been found that during mastication, when an archwire is positioned on a patient's teeth with a conventional bracket or the like, a food bolus tends to be directed towards the attachment area of the archwire to the orthodontic appliance resulting in accumulation of food with a resultant disruptive and uncomfortable forces on the archwire. The present invention provides an orthodontic appliance which is wedge shaped, and comprises a thick portion at one end and a tapering thin portion at the opposite end. The thicker portion contains at least one slot. If more than one slot is provided, they may be the same or different sizes, for receiving different characters of archwire. The design of the appliance is such that when the appliance is positioned on a patient's tooth, the receiving slots are located on the third of the crown of the patient's tooth nearest the gum, thereby applying the corrective force of the archwire adjacent the gum line to achieve more effective treatment and correction of the teeth. Moreover, the open portion of the slot is partially closed by inwardly extending toe portions to provide a smooth exterior surface, while effectively locking the archwire into position in the receiving slot.

The appliance is provided with a gradually tapering end portion opposite from the thick end, to provide an overall wedge-shaped configuration to the appliance. The tapering end gradually tapers towards the incisive edge of the tooth, such that when the device is placed on the tooth, the end tapers to a point flush with the tooth in the vicinity of the incisive edge of the tooth. The tapering end may range from a straight tapering surface to a concavely-shaped tapering surface. The tapering end serves to deflect any food bolus away from the thick end portion of the appliance, and away from the archwire which is retained by the appliance.

The appliance may be formed of any suitable material, for example metal, plastic or ceramic. In a preferred embodiment, the device is constructed from elastomeric material to cushion the shock of the force applied by the archwire.

DETAILED DESCRIPTION OF PREFERRED EMBODIMENTS OF THE INVENTION

An orthodontic appliance made in accordance with the invention is intended for direct affixation to the exterior surface of the tooth of a patient. It is well-known in the art that such affixation may be achieved by, for example, adhesive to fix the appliance to the enamel of the patient's tooth. As is known, it is often necessary to slightly etch the enamel on the crown of the tooth, for example, by using citric acid, to achieve the desired bond of the appliance to the surface of the tooth.

The orthodontic appliance is wedge-shaped in configuration, one end of the appliance being substantially thicker than the other, and the opposing end tapering to a point. The thick end of the appliance is provided with at least one receiving slot for receiving an archwire. During the course of orthodontic treatment, it is often necessary to apply varying forces, in different directions, to achieve the final desired orientation of the teeth. For this reason, a number of different slots may be provided to correctly orient the archwire (and vary the size of the archwire) to provide different corrective forces to the teeth as required in the various stages of treatment. For example, to correct gross deformities of the teeth, a direct force on the crown may be required. During later stages of treatment, it may be necessary to exert downward or sidewise forces of less magnitude. Finally, it may be necessary to simply retain the teeth in the corrected position. In this latter stage, a simplified orthodontic appliance may be employed which does not contain the additional receiving slots required to hold various archwires as in the earlier treatment stages.

Figure 1:
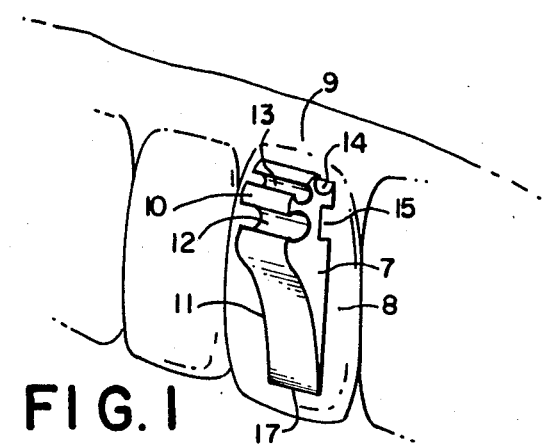
FIG. 1 is a perspective view of an orthodontic appliance made in accordance with the present invention having a concave tapering end, shown affixed to the front incisor of a patient.
Figure 2:
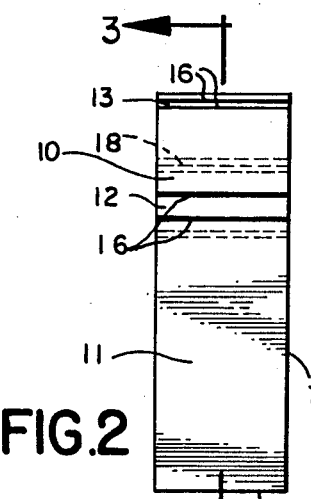
FIG. 2 is a front view of the orthodontic appliance of FIG. 1.
Figure 3:
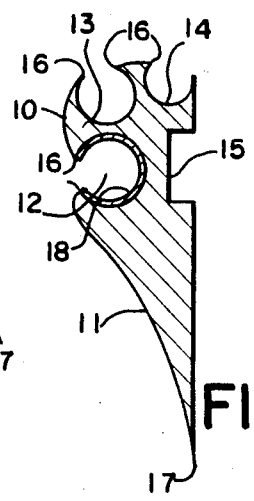
FIG. 3 is a sectional view of the orthodontic appliance of FIG. 1, taken along line 3—3 of FIG. 2.

Referring to FIG. 1, a first embodiment 7 of orthodontic appliance made in accordance with the invention is shown cemented or otherwise bonded to an anterior incisor 8 adjacent to the gum line 9. The device is wedge-shaped and comprises a thicker end generally designated at 10 and a tapering end designated generally at 11. Provided within the thicker portion 10 of the device are receiving slots 12, 13, 14 and 15, for receiving an archwire. As shown, slots 12, 13 and 14 are transverse to the longitudinal dimension of the wedge-shaped appliance 7 so as to accommodate round archwires of varying diameter, and slot 15 accommodates a rectangular archwire. As best seen in FIG. 3, the open portions of slots 12, 13 and 14 are partially closed by toe portions 16. The toe portions 16 project inwardly toward each other to secure the archwire in the slots without the need for ligating wire, and serve the further function of protecting the archwire from food bolus by restricting the entry of food particles into the slots. A rectangular slot 15 is located on the rear face of the appliance and requires that the archwire be threaded through the slot when the device is in position on the patient's tooth.

The receiving slots 12, 13, and 14 may be either the same or different in diameter, the latter as shown in FIG. 3. In a preferred embodiment, the diameter of the round slots decreases in the direction of the thick end of the appliance, as seen in FIG. 3 and correspond approximately to standard diameters of archwire. Slot 12 accomodates the largest wire, and is used for example to correct gross deformaties using maximum force. Slots 13 and 14 may be used to provide lesser and directional forces using a smaller diameter archwire. Rectangular slot 15 accomodates rectangular archwire, which is used to apply torque forces to the tooth, for example to retain the teeth in their proper orientation.

Extending from the thick portion 10 towards the incisor edge of the tooth is the tapering end portion 11. The tapering end 11 gradually tapers towards the incisive edge of the tooth, finally coming to a feather edge 17 where it is flush against the tooth as seen in FIG. 1. When so affixed to a tooth the edge 17 of the tapered end 11 may act as part of the incisive edge of the patient's tooth during mastication of food.

The tapered end 11 of the appliance serves the important function of directing any food bolus into a path away from the area of the archwire. Tapered end 11 may have either the concave shape shown in FIGS. 1 through 4, or may be straight as shown at 41 in connection with the second embodiment 37 in FIGS. 5 through 7. The effect of the tapered end 11 is to impart a backflow to food bolus which would otherwise be directed towards the archwire receiving slots.

At tapered end 11 of the appliance, the outer and inner faces meet to form an angle between the outer face and inner face of the appliance as the device tapers to form the feather edge 17, as seen in FIGS. 1 and 3. To impart the desired backflow to food bolus, the angle formed between the outer face and the inner face of the appliance as they meet to form a feather edge is substantially less than 90°.

Figure 4:
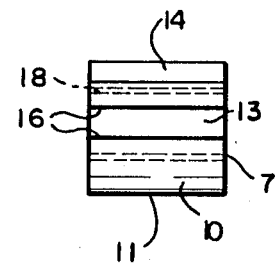
FIG. 4 is a top view of the orthodontic appliance of FIG. 1.

Further towards the desirable result of protecting the archwire from accumulation of food particles, the toe portions 16 partially closing the openings of the round receiving slots 12, 13, and 14 are rounded so as not to trap food particles. The rounded structure of the toe portions further ensures comfort to the patient by preventing laceration of the gums, cheeks, or tongue. In addition, the sides of the appliance 7 itself are rounded as shown in FIGS. 4 and 7 for the same purposes.

As seen in FIG. 1, when the appliance is affixed to the crown of the patient's tooth, the archwire receiving slots 12, 13, 14 and 15 overlie the third of the crown adjacent to the gum. The appliance 7 is affixed to the tooth 8 with the thicker end 10 of the wedge in close proximity to the gum line 9. As noted, such positioning of the archwire results in more effective bodily movement of the teeth and less tilting and tipping movements.

Figure 5:
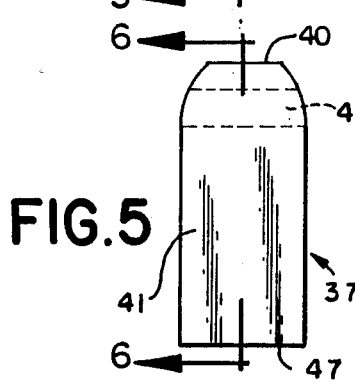
FIG. 5 is a front view of another embodiment of orthodontic appliance made in accordance with the present invention having a straight tapered edge portion.
Figure 6:
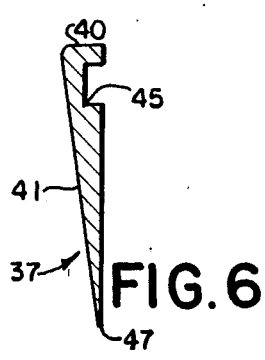
FIG. 6 is a sectional view of the orthodontic appliance of FIG. 5, taken along line 6—6 of FIG. 5.
Figure 7:
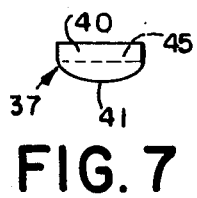
FIG. 7 is a top view of the orthodontic appliance of FIG. 5.

The embodiment of the appliance 37 shown in FIGS. 5, 6, and 7 contains only one archwire receiving slot 45. It is contemplated that this embodiment of the device be used in later stages of treatment, when only a retaining effect is needed. It is not necessary at the later stage of treatment to provide a plurality of slots for the receiving archwire. The device of FIGS. 1–4 may be removed and replaced with the less cumbersome device shown in FIGS. 5 through 7. The retaining wire or archwire is placed through aperture 45 by means of threading. Slot 45 secures the archwire by holding it against the surface of the tooth. When a twisting force is applied to the archwire the torque force is applied to the tooth adjacent the gume line. As in the previously discussed embodiment, the receiving slot 45 is placed to be in contact and apply force on the third of the exposed crown nearest the patients' gum.

It should be noted that the wedge configuration of the appliance 37 provides a straight wedge surface 41 extending from the thick end 40 to a feather edge 47 at the opposite end of the device which is closest to the incisive edge of the tooth. The straight surface 41 is effective to direct food bolus away from the archwire which is threaded through the slot 45.

The orthodontic device of the invention may be constructed of any suitable material. Metal, plastic and ceramic are all suitable materials. In a preferred embodiment as shown in FIGS. 1-4, the appliance 7 is formed of an elastomeric material to cushion the force of the archwire. When the appliance is formed of flexible elastomeric material, the receiving slot, for example the slot 12, is lined with a stainless steel tube 18 to assist in retaining the archwire in position. In the embodiment of FIGS. 5-7, the device 37 is formed of rigid material to maximize the transfer of torque from the archwire to the underlying tooth.

The size of the appliance may be varied based on the size of the patients' teeth. Generally, the thick end 10 of the appliance may be approximately 2 mm thick. By way of example, receiving slot 12 may have a diameter of 0.406 mm, and rectangular slot 15 may have a height of 0.56 mm and width of 0.406 mm. The overall length of the appliance is approximately 5 mm.

The foregoing description of the preferred embodiments of the invention are intended as illustration and not as limitation.

I claim:

1. A wedge-shaped orthodontic appliance having a first face adapted for attachment to the exposed surface of the tooth of a patient and a second face spaced from the first face substantially between opposite ends of the appliance, to define therebetween the anteroposterior thickness thereof, said appliance having a first end of substantially greater anteroposterior thickness than the opposite end, said thicker end of said appliance having at least one transverse receiving slot for receiving an archwire, and wherein the anteroposterior thickness of said appliance tapers towards said opposite end and the first and second faces meet to form an angle substantially less than 90° therebetween, said second face of said appliance being outwardly concave.

2. The orthondontic appliance set forth in claim 1 wherein the opening of said receiving slot is partially closed by extending toe portions.

3. The orthondontic appliance of claim 2 wherein the exposed edges of said extending toe portions are inwardly rounded.

4. The orthodontic appliance set forth in claim 1 wherein said appliance is formed of an elastomeric material and said receiving slot is lined with a stainless steel tube.

5. A wedge-shaped orthodontic appliance for attachment to the exposed surface of the tooth of a patient having a first end of substantially greater thickness than the opposite end, said thicker end of said appliance having a plurality of substantially round receiving slots, said slots being of different diameters, and wherein said appliance gradually tapers in thickness towards said opposite end.

6. The orthodontic appliance set forth in claim 5 wherein said slots are of progressively decreasing diameter in the direction of the thicker end of said appliance.

7. The orthodontic appliance set forth in claim 5 including at least one rectangular slot in said thicker end of said appliance.

8. The orthodontic appliance set forth in claim 5 wherein the openings of said substantially round receiving slots are partially closed by extending toe portions.

9. The orthodontic appliance set forth in claim 8 wherein the exposed edges of said extending toe portions are inwardly rounded.

10. The orthodontic applicance set forth in claim 9 wherein the exposed surface of said tapered portion of said appliance is outwardly concave.

11. The orthodontic appliance set forth in claim 10 wherein said appliance is formed by an elastomeric material and said receiving slots are lined with stainless steel.

12. The orthodontic appliance set forth in claim 11 wherein said second face of said appliance is straight.

13. The orthodontic appliance set forth in claim 12 wherein said appliance is formed of rigid material.

14. In combination with a rectangular archwire, a wedge-shaped orthodontic appliance having a first face adapted for attachment to the exposed surface of the tooth of a patient and the second face spaced from the first face substantially between opposite ends of the appliance, to define therebetween the anteroposterior thickness thereof, said appliance having a first end of substantially greater anteroposterior thickness than the opposite end, said thicker end of said appliance having at least one rectangular transverse receiving slot on the first face conforming in cross section to the rectangular cross section of the archwire for receiving and holding said archwire against the exposed surface of the tooth, and wherein the anteroposterior thickness of said appliance tapers towards said opposite end to form a feather edge which is flush against the exposed surface of the tooth.

15. A method of correcting the teeth of a patient using an orthodontlc appliance, each of said teeth having an exposed crown extending from the gum to an incisive edge, comprising:
(a) providing a wedge-shaped orthodontic appliance having a first face adapted for attachment to the exposed surface of the tooth and a second face spaced from said first face substantially between opposite ends of the appliance to define the anteroposterior thickness thereof, and having a first end of substantially greater anteroposterior thickness than the opposite end, said appliance tapering in thickness towards said opposite end to form a feather edge which is flush against the exposed crown at said opposite end, and said thicker end having at least one transverse receiving slot for receiving an archwire,
(b) affixing the first face of said appliance to the exposed crown of the tooth of the patient such that said slot in said thicker end is positioned to overlie the third of the patient's exposed crown nearest the patient's gum and the feather edge at the thinner end is positioned adjacent the incisive edge; and
(c) applying corrective force to the appliance by inserting an archwire in said receiving slot and stressing said archwire.

16. A method according to claim 15 wherein said first face is affixed to the crown with said first end immediately adjacent the gum.

* * * * *